US007883708B2

(12) United States Patent
Kosuna et al.

(10) Patent No.: US 7,883,708 B2
(45) Date of Patent: Feb. 8, 2011

(54) SUBSTANCE DERIVED FROM BASIDIOMYCETES CULTURE, METHOD FOR PRODUCING IT AND ITS USE

(75) Inventors: Ken-ichi Kosuna, Hokkaido (JP); Lan Yuan, Hokkaido (JP); Takehito Miura, Hokkaido (JP); Buxiang Sun, Hokkaido (JP)

(73) Assignee: Amino Up Chemical Co., Ltd. (JP)

( * ) Notice: Subject to any disclaimer, the term of this patent is extended or adjusted under 35 U.S.C. 154(b) by 37 days.

(21) Appl. No.: 12/149,002

(22) Filed: Apr. 24, 2008

(65) Prior Publication Data

US 2009/0004247 A1 Jan. 1, 2009

Related U.S. Application Data

(63) Continuation of application No. 09/913,283, filed as application No. PCT/JP00/08839 on Dec. 14, 2000, now abandoned.

(30) Foreign Application Priority Data

Dec. 15, 1999 (JP) ................................. 11-356267
Aug. 2, 2000 (JP) ............................. 2000-234008

(51) Int. Cl.
*A61K 36/07* (2006.01)
*A61K 36/074* (2006.01)
*A61K 65/00* (2006.01)
*A61K 38/47* (2006.01)

(52) U.S. Cl. ............................. 424/195.15; 424/94.61; 424/439

(58) Field of Classification Search ........................ None
See application file for complete search history.

(56) References Cited

U.S. PATENT DOCUMENTS

| 4,461,760 A | 7/1984 | Sugano et al. |
| 5,455,171 A | 10/1995 | Yanni et al. |
| 5,503,647 A | 4/1996 | Dahlberg et al. |
| 5,763,389 A | 6/1998 | Shen et al. |

FOREIGN PATENT DOCUMENTS

| JP | 59-41302 A | 3/1984 |
| JP | 1-258669 | 10/1989 |
| JP | 5-170756 | 7/1993 |
| JP | 6-178616 | 6/1994 |
| JP | 8-214787 | 8/1996 |
| JP | 11-89589 | 4/1999 |
| WO | WO-91/00002 | 1/1991 |
| WO | WO-95/10530 | 4/1995 |
| WO | WO-99/48386 | 9/1999 |

OTHER PUBLICATIONS

Wei et al. Proceedings of the Society for Experimental Biology and Medicine. 1995, vol. 208, No. 1, pp. 124-130.*

Barnes, Stephen, et al., "Biochemical Targets of the Isoflavone Genistein in Tumor Cell Lines," Proceedings of the Society for Experimental Biology & Medicine, vol. 208, No. 1, pp. 103-108, XP-000918092, 1998.

Choi et al., "p53-Independent Induction of P21 (Waf1/Cip10, Reduction of Cyclin B1 and G2/M Arrest by the Isoflavone Genistein in Human Prostate Carcinoma Cells," Jpn. J. Cancer Res., (2000), 91:164-173.

Coward, Lori, et al., "Genistein, Daidzein, and Their β-Glycoside Conjugates: Antitumor Isoflavones in Soybean Foods from American and Asian Diets," Journal of Agricultural and Food Chemistry, American Chemical Society, vol. 41, No. 11, pp. 1961-1967, XP 002028058, Nov. 1, 1993.

English Language Abstract of JP Publication No. 10 075739, Patent Abstracts of Japan, vol. 1998, No. 08, published Mar. 24, 1998.

English Language Abstract of JP Publication No. 56 068364, Patent Abstracts of Japan, vol. 005, No. 132, published Jun. 9, 1981.

English Language Abstract of JP Publication No. 61 009280, Patent Abstracts of Japan, vol. 010, No. 148, published Jan. 16, 1986.

English Language Abstract of JP Publication No. 61 040786, Patent Abstracts of Japan, vol. 010, No. 199, published Feb. 27, 1986.

English Language Abstract of JP Publication No. 63 208533, Patent Abstracts of Japan, vol. 012, No. 496, published Aug. 30, 1988.

Gan et al., "Medication of the Cytotoxicity of Lanostanoids and Steroids of *Ganoderma tsugae* Through Apoptosis and Cell Cycle," J. Nat. Prod., (1998) 61:485-487.

Matsuda, S. et al., *Hydrolysis of Isoflavones in Soybean Cooked Syrup by Lactobacillus casei subsp. rhamnosus IFO 3424*, J. Fermentation Bioengineering, (1992), pp. 301-304, vol. 74, No. 5.

Matsuyama, J. et al., *Hydrolytic Profiles of Soybean Isoflavone Glycoside with β-Glycosidases in the Cultures of Bifidobacteria and Lactic Acid Bateria*, Tamagawa Daigaku Kenkyu Houkoku, (1990), pp. 33-42, vol. 30, part of p. 39.

Messina, Mark J., et al., "Soy Intake and Cancer Risk: A Review of the In Vitro and In Vivo Data," Nutrition and Cancer, vol. 21, No. 2, pp. 113-131, XP008009192, 1994.

*Primary Examiner*—Vera Afremova
(74) *Attorney, Agent, or Firm*—Finnegan, Henderson, Farabow, Garrett & Dunner LLP

(57) ABSTRACT

A novel substance that has the physiological activity of the aglycone of isoflavones and the physiological activity of the culture of the basidiomycetes with the physiological activities being synergistically enhanced, obtained by cultivating a basidiomycetes having a β-glucosidase activity in a medium containing an isoflavone, a method for producing it, and food, feedstuff and medicine containing it.

The substance of the invention is improved in the physiological effect of the aglycone of isoflavones and the physiological effect of the culture of the basidiomycetes, and is not only useful as an anti-tumor agent but also is useful for therapy and/or prevention of osteoporosis and also as an immune enhancement agent.

7 Claims, No Drawings

OTHER PUBLICATIONS

Park, et al., Phytochemistry, May 1999, 51(1):147-151.
Sripuan et al., J. Sci. Fac. CMU, (1999) 26(2):59-64.
Tsuzaki, S. et al., New Food Industry, (1998), pp. 59-64, vol. 40, No. 4, Section 2 on pp. 59-60.
Yun, Taik-Koo, "Update from Asia—Asian Studies on Cancer Chemoprevention," Annals of the New York Academy of Sciences; Cancer Prevention—Novel Nutrient and Pharmaceutical Developments, pp. 157-192, XP009029523, 1999.
Zhou et al., "Inhibition of Murine Bladder Tumerigenesis by Soy Isoflavones Via Alterations in the Cell Cycle, Apoptosis, and Angiogenesis," Cancer Research, (1998) 58:5231-5238.
Jakucs, E., et al., "Some Characteristics and Partial Purification of the *Ganoderma lucidum* Cellulase System," Acta Microbiologica et Immunologica Hungarica, 1994, vol. 41, pp. 23-31.
Duran, N., et al., "A new alternative process for Kraft effluent treatment," Biodegradation, 1994, vol. 5, pp. 13-19.

\* cited by examiner

SUBSTANCE DERIVED FROM BASIDIOMYCETES CULTURE, METHOD FOR PRODUCING IT AND ITS USE

This is a continuation of application Ser. No. 09/913,283, filed Aug. 13, 2001, now abandoned, which is the National Stage of International Application No. PCT/JP00/08839, filed Dec. 14, 2000, which claims foreign priority benefit of application nos. JP 11-356267, filed Dec. 15, 1999, and JP 2000-234008, filed Aug. 2, 2000, the disclosures of all of which applications are hereby incorporated by reference in their entirety.

TECHNICAL FIELD

The present invention relates to a substance having a physiological activity such as an anti-tumor effect. More particularly, the present invention relates to a novel substance that has increased physiological activity of the aglycone of isoflavones in soybean or the like and physiological activity of basidiomycetes culture, to a method for producing it, and to a health care food composition, a feedstuff composition for animals or fish culture as well as to an anti-tumor agent as uses of the substance.

BACKGROUND ART

It has been reported that uptake of soybean or processed soybean products alleviates the risk of carcinogenesis and participates in the prevention of primary or chemical induced cancers. This effect is attributable to isoflavones contained in soybean. Soybean isoflavones have estrogen-like effects and it has been demonstrated that they have a wide variety of physiological effect to prevent cancers such as breast cancer, colorectal cancer and prostatic cancer, cardiovascular diseases, brain dysfunction, osteoporosis, alcohol dependence, menopause, hyperlipemia and the like.

As the soybean isoflavones, genistin, daidzin, glycitin and the like are known. They are glucose glycosides having genistein, daidzein and glycitein, respectively, as an aglycone. The soybean isoflavones occur in soybean seeds in the form of glucose glycoside or derivatives thereof.

The physiological effect of soybean isoflavones is mainly based on the effect of their aglycone but not glycoside. This is because they are difficult to be absorbed through the small intestine as long as they remain in that form.

Several methods for decomposing the soybean isoflavone glycosides to give their aglycone have been proposed. For example, a method of converting soybean isoflavone glycosides to aglycones by the action of β-glucosidase in soybean (Japanese Patent Application Laid-open No. Hei 1-258669), a method of extracting isoflavone aglycone produced in soy sauce cake or soy sauce oil (Japanese Patent Application Laid-open No. Hei 5-170756), a method of allowing *Aspergillus* sp. to act on soybean protein to give an isoflavone compound containing the aglycone (Japanese Patent Application Laid-open No. Hei 8-214787), a method of extracting a plant protein and then converting it to aglycone by the action of β-glucosidase or esterase (Published Translation Japanese Patent Application No. Hei 9-503781 and U.S. Pat. No. 5,763,389), a method of allowing an enzyme originated from a microbe to act on the hypocotyl of soybean to convert an isoflavone compound contained therein to its aglycone (Japanese Patent Application Laid-open No. Hei 11-89589), and so on.

Among the aglycones, in particular genistein exhibits physiological activities of tyrosine kinase inhibition, DNA topoisomerase inhibition, angiogenesis suppression and the like. In this case, however, genistein must be present in high concentrations in plasma in order to obtain sufficient physiological activities such as angiogenesis suppression. It is difficult to supply a necessary amount of genistein only by the uptake of genistin, which is a glycoside and hardly absorbed through the enteron. Consequently, in order to obtain sufficient effects of physiologic activities, the necessary amount must be taken up in the form of genistein, which is an aglycone.

On the other hand, basidiomycetes, for example, the mycelia or cultures of *Lentinus edodes* or *Ganoderma applanatum* are known to exhibit physiological effects such as immune enhancement effect and anti-tumor effect, and some of the basidiomycetes are used as anticancer agent.

In recent years, these anti-cancer agents are used mostly in combination with substances that have tumor angiogenesis inhibition effects. This is because use of substances with different mechanisms of action in combination on the same target of treatment promises high therapeutic effects.

As the substances with tumor angiogenesis inhibition effects, for example, those prepared from shark cartilage, which is a mixture of mucopolysaccharides, as a raw material, angiostatin and the like are known and some of them are put into practical use.

The term "tumor angiogenesis inhibition effects" means the effect of suppressing or inhibiting the activity of a grown tumor that produces an anigogenesis promoter by itself to generate blood vessels in order to supply nutrients and oxygen necessary for its growth.

The tumor angiogenesis inhibitor is a substance that prevents the angiogenesis of tumor cells to thereby suppresses or inhibits its hypergenesis. It is useful in the therapy of cancers since administration of it can lead to eradication of tumors.

The tumor angiogenesis inhibitor is effective when it is taken orally or intravenously injected. Currently few can be administered orally. Intravenous injection is disadvantageous since it requires a great burden on the part of patients.

The shark cartilage used for oral uptake must be taken in a large amount, for example, about 20 g or more per day but it has disadvantages that it has a fishy smell and an objectionable taste and is hard to take. For imparting the properties of suppressing the undesirable smell and taste and having it reached to the intestine without being dissolved in the stomach, which is in a strongly acidic condition, and allowing it to be dissolved and absorbed in the intestine, there have been performed cumbersome treatments. For example, shark cartilage has been pulverized to form fine powder, and such a fine powder has been coated with oil or sugar and the like.

Moreover, angiostatin has not been put into practice yet. Accordingly, a tumor angiogenesis inhibitor that can be orally administered and is highly safe is keenly demanded.

DISCLOSURE OF THE INVENTION

An object of the present invention is to solve the above-mentioned problems of the prior art and provide a novel substance that can reinforce the physiological effects of basidiomycetes culture and makes the best of the physiological activity of the aglycone of isoflavones of soybean and the like.

Further, another object of the present invention is to provide a method for producing the novel substance and health-care food, feedstuff for animals or fish culture as well as anti-tumor agents as uses of the substance.

In view of the above problems, the present inventors have made extensive study and as a result they have found that cultivation of basidiomycetes in the presence of a material that contains isoflavones, such as soybean seed and processed products thereof (i.e., isoflavones-containing material) and decomposition of the isoflavones (e.g., genistin), which are glucose glycosides, into glucose and aglycones (e.g., genistein) by the action of β-glucosidase produced by the cultivated basidiomycetes result in accumulation of the substance produced by the cultivation of the basidiomycetes together with the aglycones in the culture system. Thus, they have found that a novel substance can be obtained that has the physiological activity of the aglycone of isoflavone and the physiological activity of the culture of the basidiomycetes with the physiological activities being enhanced as compared with that of simple mixtures of the aglycone and the culture of basidiomycetes. The present invention is based on this discovery.

That is, the present invention provides the following physiologically active substances, a method for producing the same, health-care food compositions, feedstuff compositions for animals and fish culture as well as anticancer agent utilizing the same.

1) A substance having a physiological effect, comprising an aglycone of isoflavone and a cultivation product of basidiomycetes, obtained by cultivating basidiomycetes having a β-glucosidase activity in a medium in the presence of isoflavones-containing materials.
2) A substance having a physiological effect, comprising an aglycone of isoflavone and a cultivation product of basidiomycetes, obtained by cultivating basidiomycetes having a β-glucosidase activity in a medium containing a material that contains an isoflavone and β-glucosidase.
3) A substance according to 1) or 2) above, wherein the physiological activity of the aglycone of isoflavone and the physiological activity of the basidiomycetes are synergistically increased.
4) A substance according to any one of 1) to 3) above, wherein the aglycone of isoflavone is genistein.
5) A substance according to any one of 1) to 4) above, wherein the physiological effect is anti-tumor effect.
6) A substance according to 5) above, wherein the anti-tumor effect is a tumor angiogenesis inhibition effect.
7) A substance according to 5) above, wherein the anti-tumor effect is a tumor cell growth suppression effect.
8) A substance according to 7) above, wherein the tumor cell growth suppression effect is tumor cell apoptosis induction effect.
9) A substance according to any one of 1) to 4) above, wherein the material that contains an isoflavone is soybean seed, a processed product derived from soybean seed or arrowroot.
10) A substance according to 1) or 2) above, wherein the basidiomycetes that have a β-glucosidase activity is *Ganoderma lucidum* or *Lentinus edodes*.
11) A method for producing a substance having a physiological effect, comprising the steps of cultivating basidiomycetes having a β-glucosidase activity in a medium that contains a material containing an isoflavone and collecting a component that contains an aglycone of isoflavone and a cultivation product of the basidiomycetes.
12) A method producing a substance having a physiological effect according to 11) above, wherein the method comprises preliminarily cultivating the basidiomycetes to increase the β-glucosidase activity thereof, then introducing a material that contains an isoflavone in a medium, cultivating the basidiomycetes, and collecting a component that contains an aglycone of isoflavone and a cultivation product of the basidiomycetes.
13) A method for producing a substance having a physiological effect, comprising the steps of cultivating basidiomycetes in a medium that contains a material containing an isoflavone and a β-glucosidase and collecting a component that contains an aglycone of isoflavone and a cultivation product of basidiomycetes.
14) A method for producing a substance having a physiological effect according to any one of 11) to 13) above, wherein the aglycone of isoflavone is genistein.
15) A method according to any one of 11) to 14) above, wherein the physiological effect is an anti-tumor activity.
16) A method according to 15) above, wherein the anti-tumor effect is a tumor angiogenesis inhibition activity.
17) A method according to 15) above, wherein the anti-tumor effect is tumor cell growth inhibiting activity.
18) A method according to 17) above, wherein the tumor cell growth inhibiting effect is tumor cell apoptosis induction effect.
19) A method according to 11) or 12) above, wherein the material that contains an isoflavone is soybean seed, a processed product derived from soybean seed or arrowroot.
20) A method according to 11) to 13) above, wherein the basidiomycetes having a β-glucosidase activity is *Ganoderma lucidum* or *Lentinus edodes*.
21) A health-care food comprising a substance having a physiological effect according to any one of 1) to 10) above.
22) A feedstuff composition comprising a substance having a physiological effect according to any one of 1) to 10) above.
23) An anti-tumor agent comprising a substance having a physiological effect according to any one of 1) to 10) above as an active ingredient.

DETAILED DESCRIPTION OF THE INVENTION

[Production Method of Compound of Invention]

Hereinafter, the present invention will be described in detail.

The substance having a physiological effect according to the present invention can be obtained by the following method as a typical example.

That is, basidiomycetes are inoculated in a medium that comprises components such as malt extracts, yeast extracts, cellulose, ammonium tartrate and cultivated under predetermined conditions until a stage is reached where enzyme activities are increased to produce various enzymes including β-glucosidase. In this stage, an isoflavones-containing material such as soybean seeds and processed products thereof is introduced and stirred and aerated cultivation is continued under the temperature and pH conditions that give increased β-glucosidase activity to convert substantially all the isoflavone glycosides to their aglycones. Thereafter, the whole cultivation system is heated to deactivate the enzymes in the system to stop the enzymatic reaction. Further, drying and comminution is performed by lyophilization or the like means, if desired to obtain the substance of the present invention.

The isoflavones-containing material used in the present invention includes soybean seeds, defatted soybean, and a portion of appropriate tissues of them (epidermis, endosperm, hypocotyl and the like), which may be used as they are or as extracts with water, alcohols or mixtures thereof. Specific examples thereof include soybean milk. Also, isoflavones isolated from soybean seeds or the like by appropriate means may be used advantageously.

In the present invention, the term "isoflavones" include in addition to isoflavones as glucose glycosides, those glucose glycoside derivatives such as malonyl genistin and acetyl genistin, and aglycones that are components of the glucose glycosides. A material that contains any one of them is an "isoflavones-containing material" as used herein.

In the present invention, processed products produced from soybeans, defatted soybeans or the like, for example, bean pastes, soy sauces, fermented soybeans may be used as the isoflavones-containing material as far as they contain isoflavones.

Further, plants other than soybean that contain isoflavones, for example, legumes such as *Pueraria Thunbergiana*, red clover, alfalfa, *Lathyrus ugoensis*, Holland Amaranth, and *Genista*, or extracts obtained by extracting the plant tissues containing isoflavones with water, alcohols or the like may also be used as an isoflavones-containing material. In particular, arrowroot, which contains genistein in large amounts, is used advantageously.

The basidiomycetes having β-glucosidase activity used in the present invention include, for example, the following: *Lentinus edodes, Ganoderma lucidum, Grifola frondosa, Ganoderma applanatum, Pleurotus ostreatus, Flammulina velutipes, Pholiota nameko, Coriolus versicolor, Auricularia auricula, Schizophyllum commune, Grifora umbellata, Volvariella volvacea, Agaricus bisporus, Albatrellus confluens*, and *Tricholoma giganteum*.

In the present invention, the basidiomycetes mentioned above are cultivated in the presence of an isoflavones-containing material.

In the medium, in addition to the isoflavones-containing material, various carbon sources or nitrogen sources may be added. Examples of the carbon source include glucose, sucrose, maltose, saccharose, head sugar, black sugar, molasses, black strap molasses, malt extracts and the like.

Examples of the nitrogen source include meat extracts, peptone, gluten meal, soybean powder, dry yeast, yeast extracts, ammonium sulfate, tartaric acid ammonium salt, urea and the like.

Besides, inorganic salts such as sodium salts, magnesium salts, manganese salts, iron salts, calcium salts and phosphoric acid salts and vitamins such as inositol, vitamin B1 hydrochloride, L-asparagine and biotin may be added, as needed.

The cultivation may be carried out similarly to the cultivation of ordinary medium temperature microorganisms. That is, aerated cultivation being stirred at pH 2 to 6 and at a temperature of 10 to 45° C., preferably 15 to 30° C. Preferably, the cultivation is continued until substantially all of the isoflavone glycosides are converted to their aglycones. The cultivation time is usually about 4 to about 20 days, preferably about 6 to about 12 days although it may vary depending on the amount of microorganism and the form of the isoflavones-containing material.

After completion of the cultivation, the entire cultivation system is heated to deactivate the enzymes therein to stop the enzymatic reactions. The substance having a physiological activity according to the present invention can be obtained in the form of powder by concentrating mixed liquor of the culture medium and mycelia to dryness followed by pulverization. This may be fine powder obtained by drying by means of a lyophilization method followed by comminution.

In the present invention, the basidiomycetes may be used in combination with a β-glucosidase agent to reinforce the enzymatic activity of the basidiomycetes.

The enzyme agent to be used for this purpose includes enzyme preparations derived from microorganisms belonging to the genera *Aspergillus, Bacillus, Rhizopus* and the like and enzyme preparations originated from plants such as soybean, almond and the like. In the case of soybean and almond and the like, the triturates of their seeds may be used as they are.

The proportion of the isoflavones-containing material to be added to the medium of basidiomycetes has a great influence on the amount of isoflavone glycoside converted to the aglycone and sugar (or amount of genistin converted to genistein).

For example, in the case where a soybean preparation (containing 40% of isoflavones) together with a *Lentinus edodes* strain is cultivated in a medium containing malt extracts, yeast extracts and the like, a suitable concentration of the soybean preparation to be added to the medium that gives rise to a large amount of genistein converted is 3 to 10% and preferably 5% or less.

The change in the activity of β-glucosidase produced by the basidiomycetes during the cultivation gives a great influence on the generation of aglycone. Examination of changes in β-glucosidase activity and in pH of the medium after cultivating a *Ganoderma lucidum* strain in a medium similar to that mentioned above at 10 to 60° C. revealed that the β-glucosidase activity was the highest between pH 2.0 to 6.0 of the medium and a further increase in β-glucosidase activity was observed at about 40 to about 70° C.

[Pharmacological Activities]

The physiologically active substances of the present invention are not a mere mixture of a physiologically active substance that is produced by cultivation of basidiomycetes and has already been known to have anti-tumor effect and immune enhancement effect and the aglycone of an isoflavone (e.g., genistein) that has already been known to have angiogenesis suppression effect but presumably it may be an integrated substance in which the both are linked in some fashion or it may contain an unknown substance after cultivation. The reason for this presumption is that simply mixing the substance obtained by cultivating basidiomycetes in the absence of genistein with genistein fails to give rise to physiological activity (tumor angiogenesis suppression effect) equivalent to that of the substance of the present invention.

The substance produced by cultivating basidiomycetes in the absence of the isoflavones-containing material has anti-tumor effect and immune enhancement effect but does not exhibit tumor angiogenesis suppression effect.

The substance of the present invention after drying and pulverization is brown powder that has unique intense bitterness and a savory scent something like roasted soybean powder (kinako). The results of analysis of chemical composition and physiological properties thereof are shown below (refer to examples described below regarding a measurement method).

(1) Chemical Composition of the Substance of the Invention

| | | |
|---|---|---|
| 1) | Water content: | 3% or less |
| 2) | Proteins: | 7.0 to 10.0% |
| 3) | Lipids: | 5.0 to 8.0% |
| 4) | Carbohydrates: | 75.0 to 85.0% |
| 5) | Dietary fiber: | 0.5 to 2.0% |
| 6) | Ashes: | 2.0 to 5.0% |
| 7) | Isoflavones (per g of lyophilized powder): | |
| | Daidzin | 0.00 to 0.60 mg |
| | Daidzein | 28.00 to 30.00 mg |
| | Genistin | 0.00 to 0.40 mg |
| | Genistein | 55.00 to 65.00 mg |
| | Glycitin | 0.00 to 0.50 mg |
| | Glycitein | 12.00 to 15.00 mg |

(2) Physiological Properties

1) Tumor cell growth suppression effect: Suppresses growth of mouse melanoma cells, mouse colorectal cancer cells, mouse lung cancer cells, mouse angioendothelioma cells, rat breast cancer cells, human prostatic cancer cells, human bladder cancer cells and the like.
2) Tumor angiogenesis suppression effect: Suppresses mouse tumor angiogenesis.

The tumor angiogenesis suppression effect that the substance of the present invention has was confirmed by in vitro and in vivo tests using mouse tumor cells and ex ovo tests using vitelline membrane (CAM method: chorioallantoic membrane method) as described in the examples hereinbelow.

INDUSTRIAL APPLICABILITY

[Application to Medicines]

According to the present invention, substances that can be orally administered safely and with ease and have excellent physiological effects can be readily produced from inexpensive raw materials containing isoflavones.

The substances of the present invention have synergistically increased physiological effects of the aglycones of isoflavones and the cultivation products of basidiomycetes. They may be utilized not only as a therapeutic and/or preventive agent for cancers (anti-tumor agents) based on the effects confirmed by experiments but also as therapeutic and/or preventive agents for osteoporosis, menopause, cardiovascular diseases, brain dysfunction, alcohol dependence, hyperlipemia and the like, or as an immune enhancement agent and an estrogen-like substance.

Further, the substances of the present invention are produced from materials that have long since been used as food, such as mushrooms and soybean, so that no problem on safety will arise if they are taken in large amounts. They may be used also as feedstuff for animals and fish culture and health-care foods that are reinforced in the physiological activities of the aglycones of isoflavones and in the physiological activity of the cultivation products of basidiomycetes.

The substances of the present invention can be used mainly by oral route as a food, medicine and the like. The uptake amount thereof may vary depending on the age, weight, symptom, intended therapeutic effect, administration method and the like but usually it is from about 100 mg to about 5 g (on a dry basis) per dosage for an adult.

When administering the substances of the present invention, they are generally used in the form of tablets, pills, capsules, powder, granules, syrup, or the like. Appropriate auxiliary materials (starches, dextrin, sweeteners, pigments, and flavors) may be used as needed at the time of granulation, tabletting or making syrup or a coating agent.

BEST MODE FOR CARRYING OUT THE INVENTION

Hereinafter, the present invention will be described by examples and comparative examples. However, the present invention should not be construed as being limited thereto.

EXAMPLE 1

Cultivation of Basidiomycetes in a Medium Containing an Isoflavones-Containing Material (1)

(1) Materials a. Isoflavones-Containing Material
A soybean preparation containing 40% of isoflavones (produced by AHD Corp., U.S.A.), which contained the following isoflavones (per g of the preparation):

| Daidzin | 80.25 mg |
|---|---|
| Daidzein | 2.20 mg |
| Genistin | 103.94 mg |
| Genistein | 2.48 mg |
| Glycitin | 30.60 mg |
| Glycitein | 3.67 mg | b. Basidiomycetes
*Ganoderma lucidum* strain stored at 25° C. in malt extracts liquid medium by Amino Up Chemical Co., Ltd.

(2) Cultivation Conditions a. Medium

| Malt extracts (produced by Oriental Yeast Co., Ltd.) | 10.00 g |
|---|---|
| Yeast Extracts (produced by Ajinomoto Co., Ltd.) | 1.25 g |
| Water | 1 liter (l) | b. Cultivation Method

A medium was sterilized in an autoclave and stored at 4° C. before it was used. A strain of *Ganoderma lucidum* was inoculated in the medium (pH 5.5) and cultivated at 25° C. with shaking at 130 rpm. During the cultivation, the β-glucosidase activity of the culture medium was measured every other day. When the enzyme activity increased to a level higher than that when the cultivation was started, a powdered soybean preparation (isoflavones-containing material) was added to the medium to a concentration of 2.5% and the cultivation was continued further. Then, genistein and genistin contents were measured and the cultivation was terminated when it was confirmed that all the genistin was converted to genistein. After completion of the cultivation, the entire culture was heated at 121° C. for 30 minutes to complete the termination of enzymatic reaction and sterilization treatment. Then, the culture was lyophilized to produce dry powder.

The β-glucosidase activity of the culture medium was determined by reacting a β-glucosidase standard preparation (originated from yeast, produced by Oriental Yeast Co., Ltd.) with p-nitrophenyl-β-D-glucopyranoside (produced by Sigma) and measuring the absorbance at 400 nm.

The amount of isoflavones produced in the culture medium was determined by eluting an isoflavones preparation (genistin, genistein, produced by Sigma) through an ODS column (TSK gel-80™, 4.5×150 mm) with acetonitrile/water/acetic acid (10/90/0.1 →40/60/0.1) (0.8 ml/minute) according to the method of Franke, A. A. et al. (J. Agric. Food Chem. 42: 1905-1913, 1994) and measuring the absorbance at 260 nm.

The substance of the present invention obtained as stated above (Invention Substance 1) was brown fine powder and had the following properties. In the analysis hereinbelow, the moisture was measured by a 70° C. vacuum drying method. The protein was measured by a Kjeldahl method. The lipid was measured by an acid decomposition method. The dietary fiber was measured by an enzyme-weight method. The ash was measured directly by an ashing method. The carbohydrate was obtained by deduction.

a. Chemical Properties

| | | |
|---|---|---|
| 1) Moisture | | 0.7% |
| 2) Protein | | 8.8% |
| 3) Lipid | | 6.2% |
| 4) Carbohydrate | | 80.6% |
| 5) Dietary fiber | | 1.0% |
| 6) Ash | | 2.7% |
| 7) Isoflavones (per g of the lyophilized powder) | | |
| | Daidzin | trace |
| | Daidzein | 28.47 mg |
| | Genistin | trace |
| | Genistein | 59.11 mg |
| | Glycitin | trace |
| | Glycitein | 13.53 mg | b. Physiological Properties i) Tumor Cell Growth Suppression Effect (In Vitro)

Tumor cell growth suppression tests were performed using B16/BL6 mouse melanoma cells, Colon 26 mouse colorectal cancer cells, SST-2 rat breast cancer cells, T24 human bladder cancer cells, and Du145 human prostatic cancer cells. The substance of Example 1 (Invention Substance 1) was suspended in distilled water and were autoclaved. This was added to the cells in a continuously varied concentration of from 100 µg/ml to 0.1 µg/ml. Using a standard genistein preparation (produced by Sigma) dissolved in 0.1% ethanol as a positive control, the tumor cell suspension was cultivated at 37° C. for 24 hours after adjusting the tumor cell suspension to 1 to $2 \times 10^6$ cells/well with a DMEM medium containing 10% FBS. To this was added Invention Substance 1 or standard genistein preparation, and cultivation was continued for additional 48 hours. The cell growth was examined by the MTT (3-(4,5-dimethylthiazol-2-yl)-2,5-diphenyl tetrasodium bromide) method using a microplate reader. The growth suppression effect of Invention Substance 1 on various cultured cancer cells was shown in Table 1 in terms of growth suppression ratio to the tumor growth of control group with no treatment. Greater numerical values indicate higher cancer cell growth suppression effects.

TABLE 1

Growth suppression ratio (%) of Invention Substance 1 on various cultured cancers cells

| Concentration of Invention Substance 1 (µg/ml) | B-16 | Colon 26 | SST-2 | Du145 | T-24 |
|---|---|---|---|---|---|
| 12.5 | 53.7 | 11.4 | 39.6 | 27.0 | 4.3 |
| 25.0 | 72.0 | 48.7 | 36.2 | 60.0 | 31.2 |
| 50.0 | 78.5 | 78.3 | 52.9 | 85.5 | 77.9 |
| 100.0 | 86.4 | 78.8 | 61.3 | 87.4 | 98.5 |

From Table 1, it can be seen that Invention Substance 1 suppresses the growth of various cultured cancer cells in a concentration dependent fashion and exhibits high cancer cell growth suppression effect.

ii) Hemoendothelial Cell Growth Suppression Tests (In Vitro)

Mouse brain hemoendothelial cell, LE-1 cell, was preliminarily cultivated for 24 hours in a 96-well microplate coated with 1% gelatin and then treated with Invention Substance 1 in a concentration of from 10 to 0.1 µg/ml, and then further cultivated for additional 24 hours. The cell growth was detected by the MTT method. As shown in Table 2, Invention Substance 1 showed high growth suppression effect on mouse brain hemoendothelial cells in a concentration dependent fashion. From this it follows that Invention Substance 1 has hemoendothelial cell growth suppression effect, that is, angiogenesis suppression effect.

TABLE 2

Growth suppression ratio (%) of Invention Substance 1 on mouse brain hemoendothelial cells

| Concentration of Invention Substance 1 (µg/ml) | LE-1 |
|---|---|
| 12.5 | 52.4 |
| 25.0 | 63.5 |
| 50.0 | 67.6 |
| 100.0 | 76.9 | iii) 50% Growth Suppression Concentration ($IC_{50}$) of Various Tumor Cells (In Vitro): Comparison Among Invention Substance 1, Genistein Standard Preparation, and Basidiomycetes Culture 3LL mouse lung cancer cells, Colon 26 mouse colorectal cancer cells, PC3 human prostatic cancer cells, Du145 human prostatic cells, and LNCAP human prostatic cells were used and 50% suppression concentrations ($IC_{50}$) of Invention Substance 1, genistein standard preparation (produced by Sigma) and basidiomycetes culture (product obtained by cultivating basidiomycetes in the absence of isoflavones-containing material under the same conditions as in Example 1) on these cells were examined.

That is, Invention Substance 1, genistein standard preparation or basidiomycetes culture was suspended in distilled water and were autoclaved and added to the cells in a continuously varied concentration of from 1,000 µg/ml to 0.1 µg/ml. The tumor cell suspension was adjusted to $1\text{-}2 \times 10^5$ cells/well with DMEM medium containing 10% FBS and cultivated at 37° C. for 48 hours. Then, after addition of Invention Substance 1 or genistein standard preparation, the cells were further cultivated for additional 48 hours, followed by examining cell growth by the MTT method using a microplate reader. The results obtained are shown in Table 3. Lower numerical values indicate that 50% suppression of the growth of cultured cancer cells is possible at lower concentrations.

TABLE 3

$IC_{50}$ (µg/ml) of Invention Substance 1, genistein standard preparation and basidiomycetes culture on various cancer cells

| | 3LL | Colon 26 | PC3 | Du145 | LNCaP |
|---|---|---|---|---|---|
| Invention Substance 1 | 11.03 | 1.44 | 26.09 | 19.60 | 23.52 |
| Genistein standard preparation | 31.79 | 51.22 | 35.77 | 55.28 | 69.40 |
| Basidiomycetes Culture | >1000 | 3.32 | >1000 | >1000 | 377.78 |

As shown in Table 3, Invention Substance 1 exhibited high cancer cell growth suppression effect on any type of cultured cancer cell. Clearly, the growth suppression $IC_{50}$ of Invention Substance 1 on various cultured cancer cells is significantly lower than those of genistein standard preparation and of basidiomycetes culture are. This fact suggests that Invention Substance 1 is a substance what is quite different from genistein standard preparation and basidiomycetes culture.

The tumor cell growth suppression effect of Invention Substance 1 is possibly apoptosis induction of tumor cells. Accordingly, T24 cells were cultivated for 24 hours in a chamber slide in a cell number of 50,000 and Invention Substance 1 was added to the medium to a concentration of 200 µg/ml, followed by cultivation for additional 48 hours. Thereafter, the cells on the slide were fixed and stained with a TUNEL dyeing kit. As a result, the treatment with Invention Substance 1 clearly showed apoptosis of cancer cells.

iv) Tumor Cell Apoptosis Induction Effect

To confirm the tumor cell apoptosis induction effect of Invention Substance 1 on the basis of DNA, the DNA ladder specifically observed in the gene of cell that caused apoptosis was searched by electrophoresis.

Method: SST-2 (human breast cancer) was subcutaneously inoculated to SHR/NCrj rat (male, 6 weeks old) and after formation of tumor was confirmed, water containing 1% of Invention Substance 1 was administered for 2 weeks by free uptake and further water containing 10% of Invention substance 1 was orally administered for one week. A control group was allowed to freely take 0.05% $NaHCO_3$ aqueous solution for 3 weeks. Thereafter, DNA was extracted from the tumor tissue and subjected to electrophoresis to search DNA ladder. As a result, DNA ladder was clearly observed in the group administered with Invention Substance 1. This clearly indicates that Invention Substance 1 induces apoptosis on the basis of DNA.

Also, the tumor cell apoptosis induction effect of Invention Substance 1 was examined by flow cytometry that analyzes the number of cells in the phases (cell cycle) of growth, division and differentiation of rat breast cancer cells administered with Invention Substance 1 by staining nuclear DNA.

Cell cultivation: 10 ml of SST-2 rat breast cancer cells ($10 \times 10^6$ cells/ml) cultivated in a DMEM medium containing 10% FBS (fetal bovine serum) was charged in a culture dish of 10 cm in inner diameter and cultivated for 1 hour. Then, samples were added thereto as follows.

Control: DMSO (10 µl, 0.1% or Less as a Final Concentration)

Invention Substance 1 treated: Invention Substance 1 was dissolved in DMSO in a concentration of 100 mg/ml and 10 µl of the resultant solution was added to 10 ml of a cell culture medium. The final concentration of Invention Substance 1 was 100 µg/ml. After the addition of a sample, the cultivation was performed for additional 48 hours. After completion of the cultivation, the cells were recovered and the cell suspension was fixed with 70% ethanol for 24 hours. The cells were resuspended in PBS (phosphate buffered saline solution) containing 0.1% glucose and RNase (100 U/ml) at room temperature for 30 minutes. The cells were stained with propidium iodide (PI: 50 µg/ml) for 10 minutes immediately before the flow cytometry. The cell cycle of SST-2 cells treated with Invention Substance 1 was analyzed by flow cytometry.

As a result, it was found that the growth of SST-2 cells treated with Invention Substance 1 was stopped in the period (G1/S phase) from the gap (G1 phase) between the DNA synthesis and cell division and toward the DNA synthesis phase (S phase) in the cell cycle, which indicates the state where the cells could not synthesize DNA. The DNA content in G1/S phase decreased from 65.48% to 55.91% of the total amount while it increased from 1.94% to 5.20% in the cells that caused apoptosis of SST-2 cells by the treatment with Invention Substance 1. From the results it will be apparent that SST-2 cells induced apoptosis by the rest in the G1/S phase.

It has already been known that soybean isoflavones, genistein, basidiomycetes extracts and the like induce the apoptosis of cells (for example, cf. Cancer Res. 58, 5231-38, 1998; Jpn. J. Cancer Res. 91, 164-173, 2000; Biochem. Biophys. Res. Commun., 194, 944-950, 1992, J. Nat. Prod. 1998, 61, 485-487, etc.). However, as stated above, Invention Substance 1 clearly differs from genistein and basidiomycetes culture and the apoptosis induction effect of Inventive Substance 1 on cancer cells was found by the present inventors for the first time.

v) Tumor Angiogenesis Suppression Tests (In Vitro)

Angiogenesis suppression tests by a double chamber method were performed.

In the present tests, mouse colorectal cancer cell, Colon 26, was cultivated in wells of a cell cultivation plate and mouse brain hemoendothelial cell, LE-1, was cultivated in inner wells of 8 µm in diameter with perforations, the inner wells being inserted in the inside of the wells of the cell cultivation plate such that the cells were cultivated on collagen gel laid on the inner wells. The angiogenesis occurred by the stimulation of hemoendothelial cell stimulating factor produced by the colorectal cancer cells on the outside through the perforations in the bottom of the inner wells. When the angiogenesis was confirmed, Invention Substance 1 was added to the outer wells and the cultivation was performed for additional 3 days. After the cultivation, the cells on the collagen gel were photographed and the images obtained were processed on a computer. Using an image analyzing software, NIH Image, the images of hemoendothelial cells were measured for total length of lumen and number of hemoendothelial cells. Then, angiogenesis suppression ratio was calculated from the ratio of the length of lumen formed by the treated cells to the length of the lumen formed by the normal cells. The results obtained are as shown in Table 4. In the culture of cells treated with Invention Substance 1, newly formed blood vessels were greatly reduced.

TABLE 4

Tumor angiogenesis suppression effect of Invention Substance 1 (in vitro)

| | Cell Number | Length of lumen | Angiogenesis suppression ratio (%) |
|---|---|---|---|
| Non-treated cell | 22 | 1593 | — |
| Invention Substance 1 | 1 | 70 | 95.6 | vi) Tumor Angiogenesis Suppression Tests (In Vivo)

In vivo tumor angiogenesis suppression tests were performed by an under back skin method. A Millipore ring having attached on each side thereof a filter having a pore size of 0.45 µm (produced by Millipore Corp.) was filled with mouse colorectal cancer, Colon 26 ($1 \times 10^7$ cells) and transplanted under the back skin of BALB/c mouse. The animal was orally administered with 1 g/day of Invention Substance 1 and on day 5 from the transplantation of chamber, the chamber was excised and the distribution of blood vessels was recorded by photography. The photographs were input in a computer and subjected to green filter processing using an image analyzing software, NIH Image, to digitize the distribution of blood vessels and then area ratio was calculated from the area of blood vessels in the transplanted portion. The results obtained are shown in Table 5. In the mice treated with tumor cells, the area of Colon 26-induced subcutaneous blood vessels was about twice the area of blood vessels in the normal mice. On the other hand, the mice who took Invention Substance 1 had no different area of blood vessels from that of the normal mice, so that it was demonstrated that the oral uptake of Invention Substance 1 significantly suppressed tumor angiogenesis.

TABLE 5

Tumor angiogenesis suppression effect of Invention Substance 1 (in vivo)

| | Area | Area Ratio (%) |
|---|---|---|
| Normal (No treatment) | 3854 | 12.8 |
| Tumor cell-treated | 7200 | 26.9 |
| Invention Substance 1-treated | 3018 | 10.8 | vii) Angiogenesis Suppression Tests (Ex Ovo)

Ex ovo angiogenesis suppression tests were performed by a CAM (chorioallantoic membrane) method using fertilized eggs. This is a method for observing angiogenesis on a vitelline membrane and the suppression of angiogenesis can be directly observed by administering an angiogenesis suppressing substance onto egg yolk and opening the egg shell. A 10-day old egg was incubated at 37° C. and at a humidity of 60% for 3 days and then a small opening was formed in the egg shell. 3 ml of the egg white was absorbed with an injection needle and the hole was closed with a waterproof tape. On the opposite side of this hole, a window of 10×1.0 cm was formed and it was closed after formation of blood vessels on the embryo was confirmed, followed by incubation for additional 3 days. Thereafter, a sterilized phosphate buffered saline solution of Invention Substance 1 was added to the egg through the window. After incubating for additional 4 days, the egg shell was broken and the distribution of blood vessels on the vitelline membrane was recorded by photography. The photograph was input in a computer and the data of distribution of blood vessel was subjected to green filter processing using an image analyzing software, NIH Image to digitize the distribution of blood vessels. Thereafter, area ratio was calculated from the area of blood vessels in the transplanted portion. The results obtained are shown in Table 6. The treatment with Invention Substance 1 decreased the area of the blood vessels that distributed on the vitelline membrane and the suppression ratio was as high as 86.4% over normal egg. Therefore, the angiogenesis suppression effect of Invention Substance 1 was clearly demonstrated.

TABLE 6

Angiogenesis suppression effect of Invention Substance 1 (ex ovo)

| | Area | Area Ratio (%) | Suppression Ratio (%) |
|---|---|---|---|
| Normal egg (no treatment) | 87167 | 38.3 | — |
| Invention Substance 1-treated | 11862 | 5.2 | 86.4 |

EXAMPLE 2

Cultivation of Basidiomycetes in a Medium Containing an Isoflavones-Containing Material (2)

The substance of the present invention (Invention Substance 2) was obtained by performing cultivation using the raw materials described below under the same conditions as in Example 1.

(1) Materials a. Isoflavones-Containing Material

Whole grain soybean produced in Hokkaido (containing 0.730 mg/g of genistin and 0.041 mg/g of genistein, as anhydrides) was dipped in city water overnight to have water imbibed, and then folds of water was added and smothered at about 100° C. for 30 minutes, followed by removing the solids to obtain soybean milk. This contained isoflavones in the following contents.

Isoflavone Contents (µg/ml):

| | |
|---|---|
| Daidzin | 11.68 |
| Daidzein | 2.51 |
| Genistin | 45.22 |
| Genistein | 3.51 |
| Glycitin | 5.62 |
| Glycitein | 11.33 | b. Basidiomycetes

*Lentinus edodes* strain stored at 25° C. in malt extracts agar medium by Amino Up Chemical Co., Ltd.

(2) The obtained substance of the present invention (Invention Substance 2) was brown fine powder similar to Invention Substance 1 and had the following chemical and physiological properties (the measurement methods were the same as those used in Example 1).

a. Chemical Properties

| | |
|---|---|
| 1) Moisture | 0.9% |
| 2) Protein | 12.9% |
| 3) Lipid | 1.3% |
| 4) Carbohydrate | 73.9% |
| 5) Dietary fiber | 3.1% |
| 6) Ash | 7.9% |
| 7) Isoflavones (per g of the lyophilized powder) | |
| Daidzin | trace |
| Daidzein | 20.50 mg |
| Genistin | trace |
| Genistein | 37.20 mg |
| Glycitin | trace |
| Glycitein | 8.49 mg | b) Physiological Properties

In the same manner as described in Example 1, tumor cell growth suppression tests (in vitro), hemoendothelial cell growth suppression tests (in vitro), tumor angiogenesis suppression tests (in vitro), tumor angiogenesis suppression tests (in vivo), and angiogenesis suppression tests (ex ovo) were performed with respect to Invention Substance 2. The results obtained are shown in Tables 7 to 11 below.

TABLE 7

Growth suppression ratio (%) of Invention Substance 2 on various cultured cancers cells (in vitro)

| Concentration of Invention Substance 2 (μg/ml) | B-16 | Colon 26 | SST-2 | Du145 | T-24 |
|---|---|---|---|---|---|
| 12.5 | 23.2 | 7.9 | 20.8 | 17.1 | 0.0 |
| 25.0 | 52.2 | 23.9 | 58.5 | 30.0 | 9.6 |
| 50.0 | 75.4 | 41.8 | 65.4 | 37.1 | 28.1 |
| 100.0 | 86.0 | 73.3 | 84.6 | 69.8 | 54.5 |

As will be apparent from Table 7, Invention Substance 2 exhibited high suppression ratios on various cultured cancer cells and revealed that it has high cancer cell growth suppression effect.

TABLE 8

Growth suppression ratio (%) of Invention Substance 2 on mouse brain hemoendothelial cells

| Concentration of Invention Substance 2 (μg/ml) | LE-1 |
|---|---|
| 12.5 | 39.6 |
| 25.0 | 36.2 |
| 50.0 | 52.9 |
| 100.0 | 61.3 |

As will be apparent from Table 8, Invention Substance 2 revealed to have high brain hemoendothelial cell growth suppression effect in a concentration dependent fashion and clearly has angiogenesis suppression effect.

TABLE 9

Tumor angiogenesis suppression effect of Invention Substance 2 (in vitro)

| | Cell Number | Length of lumen | Angiogenesis suppression ratio(%) |
|---|---|---|---|
| Normal cell (no-treatment) | 22 | 1593 | — |
| Invention Substance 2-treated | 16 | 1366 | 14.3 |

As will be apparent from Table 9, Invention Substance 2-treated cancers showed reduced angiogenesis and exhibited suppression ratio as high as 14.3%.

TABLE 10

Tumor angiogenesis suppression effect of Invention Substance 2 (in vivo)

| | Area | Area Ratio (%) |
|---|---|---|
| Normal (No treatment) | 3854 | 12.8 |
| Tumor cell-treated | 7200 | 26.9 |
| Invention Substance 2-treated | 2494 | 10.6 |

As will be apparent from Table 10, in the mice treated with tumor cells, the area of Colon 26-induced subcutaneous blood vessels was about twice the area of blood vessels in the normal mice. On the other hand, the mice who took Invention Substance had no different area of blood vessels from that of the normal mice, so that it was demonstrated that the oral uptake of Invention Substance 2 significantly suppressed tumor angiogenesis.

TABLE 11

Angiogenesis suppression effect (ex ovo)

| | Area | Area Ratio | Suppression Ratio (%) |
|---|---|---|---|
| Normal cell (no treatment) | 97167 | 38.3 | — |
| Invention Substance 2-treated | 34300 | 14.8 | 61.3 |

As will be apparent from Table 11, the treatment with Invention Substance 2 decreased the area of the blood vessels that distributed on the vitelline membrane and the suppression ratio was as high as 61.3% over normal egg. Therefore, the angiogenesis suppression effect of Invention Substance 2 was clearly demonstrated.

COMPARATIVE EXAMPLE

Physiological Effect of a Mixture of a Basidiomycetes Culture Alone and Genistein Brown dry powder (Comparative Substance 1) was produced by performing the cultivation, lyophilization and the like operations in the same manner as in Example 1 using the same *Ganoderema lucidum* strain as in Example 1 except that the addition of the isoflavones-containing material was omitted. The chemical properties of Comparative Substance 1 (by the same analysis methods as those used in Example 1) are as follows.

Chemical Properties

| 1) Moisture | 1.6% |
|---|---|
| 2) Protein | 12.9% |
| 3) Lipid | 1.6% |
| 4) Carbohydrate | 71.4% |
| 5) Dietary fiber | 3.8% |
| 6) Ash | 8.7% |

Then, 94 g of Comparative Substance 1 was dispersed in 1 liter of water and the whole dispersion was warmed to 60° C. After adding 6 g of genistein (produced by Sigma), the mixture was stirred for 30 minutes, followed by lyophilization of the whole mixture under vacuum to obtain dry powder (Comparative Substance 2).

Invention Substance 1, Invention Substance 2, Comparative Substance 1 and Comparative Substance 2 were subjected to ex ovo angiogenesis suppression tests and in vivo anti-tumor tests using cancer-carrying mice. The ex ovo angiogenesis suppression tests were performed in the same manner as in Example 1 and the in vivo tumor growth suppression tests using cancer-carrying mice were carried out by the following method.

B-16 Melanoma cells ($1 \times 10^5$ cells) were subcutaneously transplanted to C57/BL mice and the animals were allowed to freely take one of Invention Substances 1 and 2 and Comparative Substances 1 and 2 mixed in powder feedstuff in a concentration of 5% for 21 days starting at the same time with the transplantation. On day 21, the tumor was excised from each animal and the mass was measured.

The results of these tests are shown in Tables 12 and 13 below.

TABLE 12

Comparison of angiogenesis suppression effect (ex ovo)

| | Area Ratio (%) | Suppression Ratio (%) |
|---|---|---|
| Control (No treatment) | 38.3 | — |
| Invention Substance 1 | 5.2 | 86.4 |
| Invention Substance 2 | 14.8 | 61.3 |
| Comparative Substance 1 | 27.0 | 29.5 |
| Comparative Substance 2 | 23.0 | 40.0 |

TABLE 13

Comparison of Tumor Growth Suppression of Cancer-Carrying Mice (in vivo)

| | Weight of Tumor (g in average) | Standard Deviation |
|---|---|---|
| Control (No treatment) | 1.44 | 0.59 |
| Invention Substance 1 | 0.28 | 0.32 significant to control by 0.1% or lower |
| Invention Substance 2 | 0.68 | 0.34 significant to control by 1% or lower |
| Comparative Substance 1 | 1.35 | 0.56 no significant difference from control |
| Comparative Substance 2 | 0.83 | 0.59 no significant difference from control |

As will be apparent from Tables 12 and 13, with respect to the ex ovo angiogenesis suppression effect and tumor growth suppression effect on cancer-carrying mice, Comparative Substances 1 and 2 were not so different from Control whereas Invention Substances 1 and 2 exhibited higher suppression effects than Control.

The invention claimed is:

1. A composition obtained by cultivating a Basidiomycetes in a liquid medium in the presence of isoflavone-containing materials, wherein the composition has a physiological effect and comprises:
   (a) genistein, daidzein, and glycitein, and wherein the concentration of genistein is about 55.00 to 65.00 mg per gram of dry matter of the composition;
   (b) Basidiomycetes mycelia having a β-glucosidase activity and chosen from *Ganoderma lucidum* and *Lentinus edodes*; and
   (c) dry matter of cultivation products.

2. The composition according to claim 1, wherein the composition inhibits angiogenesis.

3. The composition according to claim 1, wherein the composition suppresses tumor cell growth.

4. The composition according to claim 1, wherein the composition induces tumor cell apoptosis.

5. The composition according to claim 1, wherein the isoflavone-containing material is soybean seed, a processed product derived from soybean seed, or arrowroot.

6. A health-care food comprising the composition according to claim 1.

7. A feedstuff composition comprising the composition according to claim 1.

* * * * *